US012691051B2

(12) United States Patent
Contente Da Silva

(10) Patent No.: US 12,691,051 B2
(45) Date of Patent: Jul. 28, 2026

(54) NAIL LACQUER WITHOUT NITROSAMINE

(71) Applicant: Coty Inc., New York, NY (US)

(72) Inventor: Cleber Contente Da Silva, Barueri (BR)

(73) Assignee: Coty Inc., New York, NY (US)

( * ) Notice: Subject to any disclaimer, the term of this patent is extended or adjusted under 35 U.S.C. 154(b) by 780 days.

(21) Appl. No.: 17/905,544

(22) PCT Filed: Feb. 25, 2021

(86) PCT No.: PCT/US2021/019698
§ 371 (c)(1),
(2) Date: Sep. 2, 2022

(87) PCT Pub. No.: WO2021/178218
PCT Pub. Date: Sep. 10, 2021

(65) Prior Publication Data
US 2024/0197611 A1     Jun. 20, 2024

Related U.S. Application Data

(60) Provisional application No. 62/983,960, filed on Mar. 2, 2020.

(51) Int. Cl.
*A61K 8/73* (2006.01)
*A61Q 1/06* (2006.01)
*A61Q 1/10* (2006.01)
*A61Q 3/02* (2006.01)

(52) U.S. Cl.
CPC ............... *A61K 8/731* (2013.01); *A61Q 1/06* (2013.01); *A61Q 1/10* (2013.01); *A61Q 3/02* (2013.01); *A61K 2800/43* (2013.01); *A61K 2800/594* (2013.01); *A61K 2800/596* (2013.01)

(58) Field of Classification Search
CPC .......... A61K 8/37; A61K 8/375; A61K 8/731; A61K 8/8152
See application file for complete search history.

(56) References Cited

U.S. PATENT DOCUMENTS

2017/0145227 A1* 5/2017 Ijdo et al.
2017/0189311 A1* 7/2017 MacNeill et al.

FOREIGN PATENT DOCUMENTS

| | | | |
|---|---|---|---|
| BR | 1120220176406 A2 | 10/2022 |
| CN | 105342881 A | 2/2016 |
| CN | 115443121 A | 12/2022 |
| CN | 115443121 B | 8/2024 |
| CN | 118512340 A | 8/2024 |
| EP | 1818043 A2 | 8/2007 |
| EP | 4114345 B1 | 2/2024 |
| JP | 2018070498 A | 5/2018 |
| WO | WO2001082866 | * | 11/2001 |
| WO | WO-2021178218 A1 | 9/2021 |

OTHER PUBLICATIONS

"Chinese Application Serial No. 202180018361.7, Office Action mailed Jan. 19, 2024", w/ English Translation, 14 pgs.
"Chinese Application Serial No. 202180018361.7, Response filed Apr. 30, 2024 to Office Action mailed Jan. 19, 2024", w/ English claims, 15 pgs.
"Chinese Application Serial No. 202180018361.7, Response filed May 21, 2024 to Office Action mailed Jan. 19, 2024", W/ English Claims, 10 pgs.
"European Application Serial No. 23215282.7, Extended European Search Report mailed May 16, 2024", 5 pgs.
"International Application Serial No. PCT/US2021/019698, International Preliminary Report on Patentability mailed Sep. 15, 2022", 7 pgs.
"International Application Serial No. PCT/US2021/019698, International Search Report mailed Jun. 16, 2021", 4 pgs.
"International Application Serial No. PCT/US2021/019698, Written Opinion mailed Jun. 16, 2021", 5 pgs.

* cited by examiner

*Primary Examiner* — Robert A Wax
*Assistant Examiner* — Kimberly Barber
(74) *Attorney, Agent, or Firm* — Schwegman Lundberg & Woessner, P.A.

(57) ABSTRACT

A lacquer/polish composition for nails is disclosed and which comprises at least one a primary film former, at least one organic solvent, at least one pigment and a solvent based suspension of an alkonium sepiolite complex. The wet composition is devoid of nitrosamines or the production of nitrosamines.

18 Claims, No Drawings

NAIL LACQUER WITHOUT NITROSAMINE

CROSS-REFERENCE TO RELATED APPLICATION

This application is a U.S. National Stage Filing under 35 U.S.C. 371 from International Application No. PCT/US2021/019698, filed on Feb. 25, 2021, and published as WO 2021/178218 on Sep. 10, 2021, which application claims the benefit of priority to U.S. Provisional Patent Application Ser. No. 62/983,960 entitled "NAIL LACQUER WITHOUT NITROSAMINE," filed Mar. 2, 2020, the disclosure of which is incorporated herein in its entirety by reference.

BACKGROUND OF THE INVENTION

This invention relates to the field of nail lacquer/polish compositions comprising film forming material, organic solvent, an alkonium sepiolite complex certain non-ester plasticizers and methods of using such compositions.

Nail lacquer or polish for coating human finger and toe nails typically comprises a film forming material such as nitrocellulose, ester plasticizers such as acetyl tributyl citrate, organic solvent such as ethyl acetate, butyl acetate, toluene and/or xylene, pigment for color, and components such as clays, silicas and/or dimethyl silyl polymers as thixotropic agents to provide thickening and prevent settling of pigment. Among the clays which have been used in the art are smectite clays such as hectorite, bentonite, montmorillonite and others which have a chemical composition of hydrous aluminum phyllosilicate. The smectite clays are usually intercalated, i.e., modified, with quaternary ammonium salts or other surfactant compounds such as an amine soap, fatty sulfate, sulfonates, and/or other organic compounds to form the modified smectite clays.

When the smectite clays are intercalated with quaternary ammonium salts (hereinafter alkonium salts) the resulting intercalated alkonium aluminum phyllosilicates enable the clays to form stable suspensions in organic solvent. The exchange of alkonium salts for the naturally intercalated inorganic salts present between the lamellar microcrystalline sheets of smectite clays shifts the nature of the smectite clays from hydrophilic/ion exchange to lipophilic and enables stable suspensions in non-polar organic solvents as well as in aqueous/organic solutions. Such smectite clays intercalated with alkonium salts are very important, as discussed above, as components of nail coating compositions because they enable sustained suspension of the coating pigments and management of viscosity.

Nail lacquers and polishes typically contain amine compounds, nitrite compounds and acids associated with the pigment particles, organic color compounds, nitrocellulose, and as impurities in the clays.

It is an object of the present invention to develop a nail lacquer/polish with some kind of phyllosilicate clay that produces or develops minimal to no nitrosamine. Another object of the present invention is the development of a nail lacquer/polish that delivers essentially the same flowability and cosmetic properties as a nail lacquer/polish that has alkonium bentonite clay but minimizes and/or eliminates the production of nitrosamine.

SUMMARY OF THE INVENTION

The present invention is directed to a nail polish/lacquer composition formulated with at least one primary film forming polymer, at least one pigment, a complex of an alkonium sepiolite, and optionally non-ester based plasticizer if needed. The primary film forming polymer may be a cellulosic polymer and/or a synthetic polymer. The pigment may be solid inorganic pigment particles, organic pigment particles, organic color bodies, natural or synthetic mica, borosilicate, metal flakes such as aluminum flakes and/or similar pigment solids and combinations thereof.

The alkonium sepiolite complex comprises a sepiolite clay intercalated with at least one alkyl quaternary ammonium salt (alkonium salt) at a concentration that enables substantially permanent suspension of the alkonium sepiolite complex and pigment in the solvent system. The alkonium sepiolite provides viscosity control enabling the polish/lacquer to flow and form a uniform, wet coating and at the same time not drip or run from the coated nail. The character of the alkonium sepiolite complex, the concentration of the alkonium sepiolite complex in the composition, the concentration of intercalated alkonium salts and the minimization or absence of plasticizers minimize and/or essentially eliminate the development of nitrosamines from this composition.

The non-ester plasticizer comprises any one or more of fatty alkyl amides, fatty alkyl sulfonamides, polyepoxy amides and sulfonamides, polyethers, polyols such as polyethylene or polypropylene glycol and/or biobased plasticizers such as epoxidized fatty alcohols derived from vegetable oils including but not limited to soybean oil, linseed oil, castor oil, palm oil, epoxidized starches and sugars, fatty alcohols as well as other fatty compounds that cannot degrade or rearrange into acid moieties. The non-ester plasticizer may optionally be added to the nail polish/lacquer composition to further promote uniform distribution of the composition and to further enhance a smooth flexible character of the coating on nails when needed. Plasticizer may alternatively be eliminated when the alkonium sepiolite complex delivers sufficient, uniform and flexible character to the coating on nails.

The alkonium salt compound comprises a mono, di or tri aliphatic ammonium compound with one, two or three methyls and/or benzyl groups providing the remaining organic groups of the quaternized nitrogen. Preferably, the aliphatic quaternary ammonium compound is of vegan or synthetic origin.

The polish/lacquer composition may also contain a secondary film former such as but not limited to a synthetic polymer or resin.

Other components of the polish/lacquer composition may include surfactants, metal flakes, curable resins and monomeric compounds,

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The term "about" is understood to mean±10 percent of the recited number, numbers or range of numbers.

The term "about zero (0) wt percent" is understood to mean that no substance, compound or material to which zero (0) refers is present, up to a negligible but detectable amount is present, assuming that the detectability can be determined on a parts per million basis. Essentially no wt % or essentially no or none is understood to mean that a negligible but detectable amount is present.

In addition, where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

As used herein, the term "optionally" means that the corresponding substituent or thing may or may not be present. It includes both possibilities.

The molecular weight of a natural or synthetic polymer or derivatized natural substance such as a polysaccharide including but not limited to a cellulosic material, guar gum material and the like used according to the invention may be measured by a weight average molecular weight, and the distribution of molecules of different molecular weights of a polymer or substance used according to the invention is determined by its polydispersity index. Molecular weight is expressed as daltons (Da), kiloDaltons (KDa) and megaDaltons, which is million daltons or (MDa). The acronym $M_w$ stands for weight average molecular weight, $M_n$ is the number average molecular weight of a given polymer. Polydispersity is a unit-less number and indicates the breadth of the distribution of the polymer molecular weights and is defined as the $M_w/M_n$.

The term "alkonium salt" means a moderate to long chain mono, di or tri alkyl, alkenyl, alkadienyl and/or alkatrienyl quaternary ammonium salt compound in which each moderate to long chain aliphatic group independently is a $C_8$ to $C_{30}$ aliphatic group bound to the nitrogen and the remaining nitrogen valences are methyl and/or benzyl such that the nitrogen is bound to four organic groups and is positively charged. The nitrogen accordingly may be bound to one or two or three medium to long chain aliphatic groups and the remaining nitrogen valences may respectively be taken by three, two or one groups selected from methyl and/or phenyl. The gegenion forming the salt of the alkonium salt may be a halogen, sulfate, nitrate or phosphate, preferably chloride.

DETAILED DESCRIPTION

The present invention is directed to a polish/lacquer designed to lessen, minimize and/or eliminate the production of nitrosamine. Although not intended to be a definitive limitation of the invention, it is believed that the incorporation of a certain kind of clay and/or alkonium compound and/or their relationship in embodiments of the present invention as well as at least substantial elimination of at least certain kinds of plasticizers in embodiments of the present invention are at least in part the basis for the minimization and/or elimination of nitrosamine production by embodiments of the present invention.

According to the invention, the kind of clay complex believed to accomplish the foregoing objectives is an alkonium sepiolite complex. The alkonium sepiolite complex functions as an agent for maintaining appropriate viscosity and suspension of components, such as but not limited to solid pigment particles. Embodiments of the alkonium sepiolite complex comprise a sepiolite clay intercalated with at least one alkonium salt compound at a concentration that enables substantially permanent suspension of the alkonium sepiolite complex and at least pigment in the solvent system. The alkonium sepiolite complex provides viscosity control enabling the polish/lacquer to flow and form a uniform wet coating and at the same time not drip or run from the coated nail. The alkonium salt is a mono, di or tri aliphatic quaternary ammonium compound as defined above, is a cationic surfactant, and has sufficient emulsifier properties to maintain the alkonium sepiolite microcrystals substantially to essentially in at least semi-permanent suspension.

Sepiolite clay is known as a soft white clay mineral traditionally used for making meerschaum tobacco pipes. In contrast to bentonite and hectorite clays, sepiolite clay is a hydrated magnesium silicate clay rather than a hydrated aluminum or lithium/magnesium phyllosilicate clay. Sepiolite clay is non-expanding in aqueous media and has very small interlamellar channels while bentonite and hectorite clays are expanding (form gels) in aqueous media and have relatively large interlamellar channels. Because of the non-expanding, narrow lamellar channel microcrystalline layer arrangement of sepiolite clay, adsorption of the alkonium cations is believed to occur at least in part on external particle surfaces rather than entirely upon intercalation surfaces. See "Cosmetic ingredient Review", Safety assessment of alkonium clays as Used in Cosmetics, Mar. 7, 2016, Lilian C. Becker. The character of the alkyl group(s) of the alkonium salt compound, its concentration and its complexation with sepiolite are believed at least in part to minimize and/or essentially eliminate the development of nitrosamines from nail coating compositions based upon nitrogen containing film formers.

Preferably, the sepiolite clay obtained from commercial sources is further purified (e.g., re-purified) for use in the complex. The purification step or steps minimize and/or eliminate impurities and natural substances present in the sepiolite clay as mined. The purification can be accomplished by treating a portion of the sepiolite clay with hot aqueous or aqueous alcohol medium while applying high sheer stirring to form a hot dispersion, filtering the hot dispersion, removing the resulting first filtrate, cooling the liquid and filtering to yield an additional second filtrate, examining for purities of the first and second filtrates, optionally extracting the first and second filtrates separately or together with aqueous acid while warming same and optionally and separately extracting with base while optionally warming same, cooling and filtering to yield a third filtrate, drying the filtrate under heat and vacuum to produce purified sepiolite clay The alkonium salt compound, which is also known as an aliphatic quaternary ammonium compound comprises a $C_8$ to $C_{30}$ mono, di and/or tri-aliphatic group in which each aliphatic group is independently selected so that a di or tri-aliphatic ammonium compound may have two or three different aliphatic groups. Each aliphatic group may be an alkyl, alkenyl, alkadienyl and/or alkatrienyl group of 8 to 30 carbons. The remaining valences of the nitrogen of the ammonium compound are taken up by three, two or one methyls and/or benzyl groups respectively. The alkonium salt compound may also be a mixture of thereof. Preferably, the alkonium compound is a mono or di aliphatic ammonium compound in which each aliphatic group independently is a $C_{10}$ to $C_{26}$ alkyl, alkenyl, alkadienyl and/or alkatrienyl group with the remaining valences being taken by three or two methyls and/or benzyl groups and/or a mixture of any of the mono or di substituted ammonium compounds More preferably, the alkonium compound has two aliphatic groups in which each aliphatic group independently is a $C_{14}$ to $C_{20}$ di-alkyl, alkenyl and/or alkadienyl group. The remaining nitrogen valences are taken by two methyls and/or benzyl groups. The more preferred alkonium compound may also be a mixture of any of the di substituted ammonium compounds. Especially more preferably, the alkonium compound is a $C_{14}$ to $C_{20}$ mono-alkyl, alkenyl and/or alkadienyl ammonium compound with three methyls and/or benzyl groups also bonded to the ammonium nitrogen and or a mixture of any of the mono substituted ammonium compounds. Most preferably, the alkonium compound is mixture of any two or more of the $C_{14}$ to $C_{20}$ mono and/or di-alkyl, alkenyl, alkadienyl and/or alkatrienyl ammonium compounds with three or two methyls and/or benzyl groups also bonded to the ammonium nitrogen. An exemplary alkonium compound is one of, or a mixture of, the $C_{14}$ to $C_{20}$ mono and/or di-alkyl, alkenyl, alkadienyl and/or alkatrienyl ammonium compounds with three or two methyls and/or benzyl groups also bonded to the ammonium nitrogen. Another exemplary alkonium compound is a mono $C_{14}$ to $C_{20}$ alkyl or alkenyl, dimethyl ammonium salt compound. Preferably, the aliphatic groups are saturated rather than unsaturated.

Preferably, the alkonium compound is of vegan or synthetic origin. The vegan alkonium compound may be prepared from saponified olive oil, soybean oil, rape seed oil, palm oil, coconut oil and similar plant seed oils by converting the corresponding fatty acid or fatty acids to fatty amine compounds and quaternizing by adding additional fatty groups and/or methyl and/or benzyl groups to the fatty amine. Synthetic alkonium compounds may be prepared by similar conversion of fatty acids derived from petroleum.

The alkonium sepiolite complex may be prepared by combining a measured amount of dried, finely powdered sepiolite clay in an alcohol or aqueous alcohol medium, addition of an excessive amount of the alkonium compound and mixing the slurry with a high speed mechanical mixer for a sufficient time to enable adsorption of at least some of the alkonium compound onto the sepiolite clay powder. Typically, the time required may range from 10 to 90 minutes at ultra-high speed sheer mixing. The slurry is filtered and the solid, wet, powdered filtrate collected and dried with moderate heat no higher than 100° C. When an aqueous alcohol medium is used, the resulting alkonium sepiolite complex will also contain a variable amount of intercalated water. The preferred medium is aqueous alcohol at a concentration of at least about 50 wt percent to 95 wt percent alcohol. The presence of water enables more facile displacement of the intercalated inorganic cations relative to the use of an alcohol only medium. At least a twenty percent excess of alkonium compound relative to the theoretical amount capable of being adsorbed by the powdered sepiolite clay is used to shift the adsorption equilibrium toward clay adsorption The concentration of the alkonium compound in the alkonium sepiolite may be in the weight range of about 0.5 weight percent to about 8 weight percent, preferably about 0.5 weight percent to about 4 weight percent, more preferably about 0.5 weight percent to about 2 weight percent relative to the weight of the sepiolite clay without the alkonium compound. The dry sepiolite clay weight is measured after heating, drying and pulverizing the clay before its combination with the alkonium compound. The weight of the alkonium compound in the complex is measured by subtraction after the wet alkonium sepiolite complex is filtered and the filtrate dried under moderate heat to provide dry alkonium sepiolite complex. The weight of the dry sepiolite clay before addition of the alkonium compound is subtracted from the weight of the dried quaternized sepiolite complex to provide the weight of the added alkonium compound.

The primary film former may be a cellulose derivative and/or a synthetic polymer. Exemplary film formers include but are not limited to cellulose acetate, cellulose acetate butyrate, ethyl cellulose, vinyl polymers, nitrocellulose, methacrylate and acrylate type polymers and co-polymers, and mixtures thereof. The preferred primary film forming compound for use in the present invention is nitrocellulose which provides a combination of properties of toughness, durability, solubility and solvent release.

It has been discovered that primary film formers having higher molecular weights will produce films having a mirrorlike appearance. In this regard, as the molecular weight of the film forming compound increases, the mirrorlike appearance of the resulting lacquer/polish film can be improved. For example, use of the preferred film former, nitrocellulose, having an average molecular weight of greater than 56,000 can show improvements in mirror appearance. Nitrocellulose as a primary film former is available from a variety of sources, for example, Hercules, Inc. in various molecular weights. These grades of nitrocellulose include nitrocellulose RS1/2 sec. having a weight average molecular weight of 56,000, nitrocellulose RSS-6 sec. having a weight average molecular weight of 112,000, nitrocellulose RS15 sec. having a weight average molecular weight of 130,000, nitrocellulose RS60-80 sec. having a weight average molecular weight of 175,000, nitrocellulose RS150 sec. having a weight average molecular weight of 190,000, as well as other grades having both lower and higher molecular weights.

While higher weight average molecular weights of primary film formers such as nitrocellulose provide mirror-like coatings, these higher weights also contribute to increased viscosity. In embodiments of the lacquer/polish composition of the present invention, the concentrations and weight average molecular weights of the primary film former and the alkonium sepiolite complex are preferably balanced to provide a combination of viscosity and fluidity that enables suspension of the pigment particles and/or organic pigment, minimizes and/or prevents run-off and enables development of coating leveling so as to produce a smooth substantially uniform coating.

The concentration of the alkonium sepiolite complex in the lacquer/polish composition including solvent may range from about 0.1 wt percent to about 12 wt percent, preferably from 0.2 wt percent to about 6 wt percent, more preferably 0.4 wt percent to about 3 wt percent, especially more preferably up to no more than about 0.5 to 2 wt percent and most preferably about 0.3 to about 1.3 wt percent relative to the total weight of the composition. The concentration of the alkonium sepiolite complex will depend at least in part upon the concentration of the pigment and other materials of the composition that are not soluble in organic medium. As mentioned above, the alkonium sepiolite complex maintains and stabilizes the suspension of the pigment and solvent insoluble materials in the composition.

The concentration of the primary film former may range from about 4 wt percent to about 45 wt percent, preferably from about 4 wt percent to about 35 weight percent, more preferably about 4 wt percent to about 25-30 wt percent relative to the total weight of the composition. As mentioned above, the concentration of the primary film former is balanced with the concentration of the alkonium sepiolite complex. For the primary film use of too small an amount tends to result in the coated films being easily damaged while use of too large an amount can result in the coated film being too hard and brittle, which easily causes undesirable peeling and hence poor wear resistance. Therefore, preferably lacquer/polish compositions of the present invention include primary film forming polymers and combinations thereof in an amount ranging from about 11 to about 30 wt percent, and preferably in the range of about 13 to about 25 weight percent of the lacquer/polish composition. These weight percentages are preferably applicable when the primary film former is the preferred nitrocellulose.

In addition to the primary film formers, embodiments of the lacquer/polish compositions of the present invention may also include one or more secondary film formers effective to strengthen the primary film former and to provide the composition with additional gloss and adhesion characteristics. Exemplary secondary film formers which may be used in the present invention include, for example, drying and non-drying alkyd resins, polyvinyl resins for example polyvinyl acetate, polyester resins, acrylic polymers and copolymers, maleic modified glycerol esters of rosin and aromatic amide epoxy resins such as toluene sulfonamide epoxy resin and tosylamide epoxy resin. Additionally, or alternatively, embodiments of the lacquer/polish compositions of the present invention may include aldehyde condensation products such as arylsulfonamide formaldehyde resins, specifically toluene sulfonamide formaldehyde resin which is a condensation product of formaldehyde and toluene sulfonamide although formaldehyde resins are not favored because of the irritation and toxicity of formaldehyde derivative residues. These secondary film formers may be added to embodiments of the lacquer/polish compositions of the present invention to strengthen and add acceptable wear characteristics to the primary film former. In general, the amount of secondary film former and combinations thereof range from about 3 to 15% by weight of the composition, and preferably about 5 to 10% by weight of the lacquer/polish composition.

In addition to the primary and secondary film formers, embodiments of the lacquer/polish compositions according to the present invention may also include certain plasticizers to plasticize the primary film forming polymer and provide a flexible nail coating. However, while some plasticizers may ameliorate the production of nitrosamines, other plasticizers exacerbate the production of nitrosamine over time when present in film former nail coatings. Exacerbation is developed when ester plasticizers are included in the composition. Embodiments of ester plasticizers include, for example, dicresyl phosphate, dibutyl tartrate, benzyl benzoate, 2, 2, 4-trimethyl-1, 3-pentanediol diisobutyrate, dibutyl phosphate, butyl acetyl ricinoleate, butyl glycolate, butyl stearate, diphenyl phosphate, camphor, castor oil, and phthalate type plasticizers, for example, diamylphthalate, dibutyl phthalate, diethyl phthalate, dioctyl phthalate, dibutoxy ethylphthalate, triesters, tetra esters such as sucrose acetate isobutyrate, triethyl citrate, acetyl trialkyl citrates such as acetyl tributyl citrate ester, other tri and tetra esters of citric, polyol triesters of acetic, butyric, valeric, stearate, phthalic, oleic, butyric and benzoic acids, and the polyol may be triols and tetraols of C2 to C10 alkanes, such as glycerol, butyl triol and similar polyols and more lipophilic esters and mixtures thereof. While not being a limitation of the invention, it is believed that ester plasticizers as least in part degrade when present over a period of time in the liquid nail polish/coating composition when alkonium bentonite and/or alkonium hectorite clays are present. The degradation is believed to release acid which along with the alkonium bentonite or hectorite is believed to co-catalyze the nitrogen conversion process likely leading to production of nitrosamine.

Suitable plasticizers include non-ester plasticizers such as fatty alkyl tolylsulfonamide, fatty alkyl phenylsulfonamide, tosylamide polyepoxide, epoxidized fatty alcohols derived from vegetable oils such as palm oil, soybean oil, linseed oil, coconut oil, olive oil, rice bran oil, rapeseed oil, cocoa butter, mineral oil and C10-C30 saturated and unsaturated aliphatic alcohols which may contain at least one hydroxyl group and/or multiple hydroxyl groups. Additional non-ester plasticizers include polyether and polyol compounds such as polyethylene glycol, polypropylene glycol and similar polyether and sulfonamide plasticizers. Suitable plasticizers included in embodiments of the compositions of the present invention are present in amounts sufficient to provide acceptable flexibility to the dried/cured lacquer/polish composition on the human or synthetic nail surface. Preferably, the concentration of the plasticizers for use in embodiments of the lacquer/polish compositions of the present invention range from about 0.1 to 20 percent by weight, preferably about 0.1 to about 8-10 percent, more preferably about 0.1 to about 3-6 percent by weight relative to the total weight of the liquid nail enamel composition, i.e., the composition in liquid form with solvent and/or volatile liquids.

The lacquer/polish compositions of the present invention may include one or more solvents and/or volatile liquids such as those generally used in conventional lacquer/polish and/or nail enamel compositions. Examples of these solvents include ethyl acetate, methyl acetate, methanol, ethanol, isopropanol, diacetone alcohol, propyl acetate, acetone, methyl ethyl ketone, methyl butyl ketone, n-butanol, xylene, aromatic (containing phenyl groups), ethers, ketones, toluene, alkanes for example, pentane, cyclopentane, hexane, heptane, cyclohexane, cyclic ethers for example, tetrahydrofuran and 1,4-dioxane, cellosolve (2-ethoxyethanol, i.e., ethyl glycol ether), butyl cellosolve acetate, cellosolve acetate, methyl cellosolve acetate, butyl cellosolve, ethyl cellosolve, glycol ethers such as ethers of ethylene glycol and propylene glycol, phenylated solvents for example, xylene, chlorinated hydrocarbons for example, methylene chloride, chloroform and methylchloroform. Esters of organic acids such as acetic acid for example, methyl acetate, ethyl acetate, n-butyl acetate may be included but preferably would be used in minimal amounts because of the possibility of their decomposition at least in part to produce acids. The aforementioned solvents can be used alone or in mixtures thereof. In general, the amount of solvent used in the compositions of the present invention range from about 44 to 85% by weight, and preferably from about 50 to 75% by weight of the lacquer/polish composition.

For the lacquer/polish compositions according to the present invention, embodiments also include pigment particles such as but not limited to organic pigments and inorganic pigment particles, metallic microflakes and similar solid particulate coloring substances. One or more known liquid, semi-liquid and/or gel organic colorants may also be added to these compositions. Pigments are added to the composition to provide cosmetically acceptable shades and to pacify the films. Pigments for use in the present invention may include any of those pigments which are generally known for use in lacquer, polish and/or enamel compositions. For example, these pigments can include cosmetic grade or purified titanium dioxide, yellow and red iron oxides, bismuth oxychloride, iron blue, iron black, mica particles, ultramarine blue, D&C Red #7, chromide oxide greens, carbon black and lampblack. Other pigments which may be used in compositions according to the present invention may include the Lake pigments, for example, D&C Red #6 barium Lake and D&C Red #7 calcium Lake synthetic mica, D&D Red 34, D&C Yellow 5 Lake, Black 2, and ferric complexes.

In addition to the foregoing pigments, embodiments of the lacquer/polish compositions may also include titanated micas, polyethylene teraphthalates and pearl essence which is a suspension of crystalline guanine in nitrocellulose and solvents, as well as other additives which will affect the appearance of the pigment. Although the amount of pigment in the compositions of the present invention will vary as a function of the type of pigment and other components included in the composition, in general, pigments can be included in an amount up to about 10% by weight of the lacquer/polish composition.

Anti-foaming and leveling agents are also suitable for use in the lacquer/polish compositions of the invention. Examples of satisfactory anti-foaming and/or leveling agents include dimethicone available from Dow Corning, identified as Dow Corning 200; nonionic acetylenic diol surfactant available from Air Products and Chemicals, Inc. under the mark Surfynol 104 Surfactant and the ethoxylated analogs under the marks Surfynol 440, 465 and 485 surfactants, and Surfynol DF-110 defoamer series; as well as a number of foam destroying silicon free polymers, polysiloxanes, polysiloxane copolymers and mixtures thereof available from BYK-Chemie, USA under the marks BYK-052 (silicon free), BYK-053 (silicon free), BYK-065, BYK-070 and BYK-80. The preferred anti-foaming/leveling agent for use in accordance with the present invention is dimethicone.

Optionally, an organic dicarboxylic acid such as malonic, maleic, succinic, malic, citric, glutaric, adipic acid and/or a C2-C10 alkanodioic acid may be included in the lacquer composition. A typical concentration of the diacid, if used, may range from 0.01-0.2 wt %. The diacid may be included if enhanced adhesion of the coating to the nail surface is desired. Nevertheless, inclusion of diacid preferably is avoided for the reasons given above in regard to nitrosamine production.

Although examples described herein are directed towards nail lacquer/polish compositions, it also stands to reason that sepiolite can be included in other cosmetic compositions. For example, sepiolite can be included in a foundation composition, a lipstick or lip gloss composition, or a mascara composition.

EXPERIMENTAL

Preparation of Test Samples

A series of nail lacquer/polish test samples were prepared with nitrocellulose as the primary film former. The Base formulation for the samples included about 45 wt percent nitrocellulose and a remaining percentage of a solvent mixture of butyl acetate, ethyl acetate and isopropyl alcohol. The samples were prepared with and without the ester plasticizer acetyl tributyl acetate. The nail lacquer test samples were prepared by high shear blending approximately 20 wt percent of the base formulation, a mixture of ethyl and butyl acetate at about 70-75 combined wt percent and approximately 6 wt percent of the following alkonium clay mixtures (each alkonium clay mixture was approximately 10 wt percent of the alkonium clay, about 85 wt percent butyl acetate and about 5 wt percent isopropyl alcohol). The red pigment mixture was approximately 2 wt percent rouge covachip, about 10 wt percent ethyl cellulose and about 2 wt percent acetyl tributyl acetate in isopropyl alcohol and was assayed without further combination with alkonium clay or other film former.

A. hectorite with acetyl tributyl acetate in ethanol

B. hectorite without acetyl tributyl acetate in ethanol

C. bentonite with acetyl tributyl acetate in ethanol

D. bentonite without acetyl tributyl acetate in ethanol

E. sepiolite without acetyl tributyl acetate in isopropanol

F. red pigment with acetyl tributyl acetate in isopropanol with ethyl cellulose.

G. Base

The hectorite, bentonite and sepiolite clays were alkonium clay complexes with a mixture of mono stearyl and oleyl dimethyl benzyl ammonium chlorides produced from tallow glycerides. The sepiolite mixture was formed with additional isopropanol instead of ethanol and a higher rate of shear mixing to form suspensions. No pigment was included in these formulations.

Each final formulation was homogenized by high shear force mixing, subsequently placed into a container and allowed to rest for approximately one week and then tested for the presence of nitrosamine. Nitrosamine analysis was conducted using the EPO Method 521.1. This method employs a GC/MS (gas chromatograph/Mass Spectrometer) analysis and identification method. To conduct the test, each resting formulation was filtered to remove solids and an appropriate aliquot of the filtered liquid injected into the GC/MS apparatus. A read out of the mass signatures of each chromatographic peak and comparison to peak standards provided the identity and quantity of each nitrosamine detected. Each sample was tested immediately after preparation (rest period about 5 to 10 minutes) and after 2 months at 45° C. The base formulation with pigment and the base formulation alone were examined by the GC/MS method to establish that the nitrosamines result in the presence of the alkonium smectite clay complex. The base formulation alone establishes a null standard. Table I presents the results of nitrosamines in parts per million (ppm) in each sample. The lower limit of the analysis was 4 ppm. NDELA is nitrosodiethanolamine, NDMA is nitrosodimethylamine. NMEA is nitrosomethylethylamine. Misc is miscellaneous nitrosamine compound.

TABLE I

| Sample | NDELA | NDMA | NMEA | Misc Nitrosamine | Total |
|---|---|---|---|---|---|
| A—fresh | <10 | 75 | <4 | <4 | 75 |
| A—2 months | 21 | 3680 | <4 | <4 | 3693 |
| B—fresh | <10 | 100 | <4 | <4 | 100 |
| B—2 months | 11 | 941 | <4 | <4 | 941 |
| C—fresh | <10 | 4187 | <4 | <4 | 4229 |
| C—2 months | 23 | 6632 | <4 | <4 | 6651 |
| D—fresh | <10 | 1552 | <4 | <4 | 1560 |
| D—2 months | <10 | 666 | <4 | <4 | 666 |
| E—fresh | <10 | <4 | <4 | <4 | 0 |
| E—2 months | <10 | 12 | <4 | <4 | 12 |
| F—fresh | <10 | <4 | <4 | <4 | 0 |
| F—2 months | <10 | <4 | 17 | 7 | 24 |
| G—fresh | <10 | <4 | <4 | <4 | 9 |
| G—2 months | 67 | 25 | <4 | 36 | 61 + 67 |

The results indicate that the ammonium compounds of the alkonium bentonite and hectorite clays combine with nitrosating agent impurities in the nitrocellulose and in the clays under heat and optionally acidic media to form nitrosamines. The results also demonstrate that ester plasticizers such as acetyl tributyl acetate and acetyl tributyl citrate co-catalyze nitrosamine production when the alkonium clays are present. These results show that:

1) the nitrocellulose formulation without the alkonium bentonite and hectorite clays (Base Formulation) does not produce significant nitrosamine;

2) the nitrocellulose formulation with alkonium bentonite clay or hectorite clay with ester plasticizer produces significant nitrosamine and the production is exacerbated over time;

3) the nitrocellulose formulation with alkonium bentonite clay or hectorite clay but without ester plasticizer also produces significant nitrosamine but the production is not exacerbated over time;

4) the base nitrocellulose formulation without the alkonium bentonite and hectorite clays does not produce nitrosamines;

5) the pigment formulation containing a film former that is not nitrocellulose and containing no alkonium clay complex does produce nitrosamine; and, 6) the nitrocellulose formulation with alkonium sepiolite complex instead of alkonium bentonite or alkonium hectorite minimizes and/or eliminates the production of nitrosamines from the subject lacquer/polish formulation.

Together, these results demonstrate that the "activator" for nitrosamine formation in nitrocellulose lacquer/polish formulations is the alkonium bentonite and hectorite clays and the inclusion of ester plasticizer exacerbates nitrosamine over time but substitution of an alkonium sepiolite complex negates the nitrosamine production.

Exemplary Nail Lacquer Composition

A final nail lacquer composition may be prepared by combining two separately prepared intermediate mixtures. The first intermediate mixture is prepared by combining about 44-46 wt % butyl acetate, about 10-11 wt % ethyl acetate and about 45 wt % of a solution of NQ prisma cotton (nitrocellulose) at 30 wt % in isopropyl alcohol. The mixture is rapidly stirred until a uniform, homogeneous solution is produced, hereinafter the Prisma mixture. The second intermediate mixture comprises a vegan sepiolite complex in a mixture of alkyl acetate solvents. The vegan sepiolite complex includes purified sepiolite clay intercalated with a mixture of fatty quaternary ammonium chlorides produced from coconut and/or palm oil fatty acids in which the carboxylic acid groups have been converted to primary amine groups and the amine groups quaternized with methyl groups. The second intermediate mixture is formulated by combining the intercalated sepiolite with a mixture of butyl and ethyl acetates and high shear blending the mixture to provide an emulsified dispersion (hereinafter the sepiolite dispersion) which at a final weight of 4-6 wt % relative to the total weight of the lacquer composition will deliver about 0.1 to 0.3, preferably about 0.2 wt % sepiolite complex in the final lacquer composition.

The final lacquer composition is prepared by combining about 4-6 wt % of the sepiolite dispersion delivering about 0.2 wt % sepiolite complex with about 30-36 wt % of the Prisma mixture, about 24-26 wt % butyl acetate, 24-26 wt % ethyl acetate and 10-14 wt % of a pigment mixture of brown, red or blue pigment particles (about 30 wt %) in ethyl cellulose (about 69 wt %) and non-ester surfactant (about 0.1-0.5 wt %). The combined mixture may be blended under high shear conditions to provide a uniform, homogeneous, final lacquer composition.

The final lacquer composition may be assayed for its ability to deliver a smooth, flexible coating on nails by applying an aliquot of the composition to an artificial nail substrate. The composition on the substrate is allowed to dry and the resulting coating is examined visually for uniformity and smoothness. The coated substrate may be flexed multiple times to assess the flexibility of the coating. If cracking and/or flaking and or peeling is observed, additional plasticizer such as a polyepoxy amide, PEG 20-50 or epoxidized fatty alcohol in a mixture of ethyl and butyl acetates may be added to the final lacquer composition. The wt percent of the plasticizer in the plasticizer-solvent solution is calculated to provide about 0.1 to 0.3 wt % of the plasticizer in the final composition.

Another example of a lacquer composition was prepared according to Table 2. The formulation shown in Table 2 demonstrated good stability after three months in that no sedimentation was observed.

TABLE 2

| Ingredient | Amount (wt %) |
|---|---|
| Butyl Acetate | 50-60 |
| Ethyl Acetate | 4-8 |
| Sepiolite Clay | 4-8 |
| Solution NQ Prisma System 2105 | 16-20 |
| Acetyl Tributyl Citrate | 1-5 |
| Tosylamide Epoxy 75TFF Resin | 3-7 |
| Silica-CABOSIL TS610 | 2-6 |

Exemplary Foundation Formulation

An example of a foundation composition is shown below in Table 3.

TABLE 3

| INCI Name | WT/WT % |
|---|---|
| DICAPRYLYL CARBONATE, TOCOPHEROL | 7-10% |
| DICAPRYLYL ETHER, TOCOPHEROL | 7-10% |
| ETHYLHEXYL METHOXYCINNAMATE | 1-4% |
| DICAPRYLYL ETHER, DICAPRYLYL CARBONATE, TRI(POLYGLYCERYL-3/LAURYL) HYDROGENATED TRILINOLEATE, CETYL PEG/PPG-10/1 DIMETHICONE, TRIETHOXYCAPRYLYLSILANE, PENTAERYTHRITYL TETRA-DI-T-BUTYL HYDROXYHYDROCINNAMATE, IRON OXIDES | 0.4-0.8% |
| DICAPRYLYL DICAPRYLYL ETHER, DICAPRYLYL CARBONATE, TRI(POLYGLYCERYL-3/LAURYL) HYDROGENATED TRILINOLEATE, CETYL PEG/PPG-10/1 DIMETHICONE, TRIETHOXYCAPRYLYLSILANE, PENTAERYTHRITYL TETRA-DI-T-BUTYL HYDROXYHYDROCINNAMATE, IRON OXIDES | 0.1-0.4% |
| DICAPRYLYL ETHER, DICAPRYLYL CARBONATE, TRI(POLYGLYCERYL-3/LAURYL) HYDROGENATED TRILINOLEATE, CETYL PEG/PPG-10/1 DIMETHICONE, TRIETHOXYCAPRYLYLSILANE, PENTAERYTHRITYL TETRA-DI-T-BUTYL HYDROXYHYDROCINNAMATE, IRON OXIDES | 0.07-1% |
| TRIETHOXYCAPRYLYLSILANE, TITANIUM DIOXIDE (CI 77891) | 6-8% |
| TRIMETHYLSILOXYSILICATE | 2-6% |
| Z-COTE HP1 (30083072) | 1-4% |
| silica | 1-3% |
| Mica and Methicone | 0.5-1% |
| ALUMINUM STARCH OCTENYLSUCCINATE | 1-4% |
| Sepiolite Clay | 1-3% |
| Propylene Carbonate | 0.4-0.8% |
| WATER, DICAPRYLYL ETHER, DICAPRYLYL CARBONATE, SODIUM CHLORIDE, TRI(POLYGLYCERYL-3/LAURYL) HYDROGENATED TRILINOLEATE, CETYL PEG/PPG-10/1 DIMETHICONE, SODIUM BENZOATE, PENTAERYTHRITYL TETRA-DI-T-BUTYL HYDROXYHYDROCINNAMATE. | 40-60% |
| WATER, DICAPRYLYL ETHER, DICAPRYLYL CARBONATE, GLYCERIN, SODIUM CHLORIDE, TRI(POLYGLYCERYL-3/LAURYL) HYDROGENATED TRILINOLEATE, CETYL PEG/PPG-10/1 DIMETHICONE, SODIUM BENZOATE, PENTAERYTHRITYL TETRA-DI-T-BUTYL HYDROXYHYDROCINNAMATE. | 5-15% |
| WATER, GLYCERIN, SILYBUM MARIANUM SEED EXTRACT | 0.05-2% |
| ALOE BARBADENSIS LEAF JUICE | 0.05-0.2 |
| Fragrance | 0.1-0.5% |

TABLE 3-continued

| INCI Name | WT/WT % |
|---|---|
| Chlorophenesin (Vegan) | 0.1-0.5% |
| WATER, DEIONIZED | 0.1-0.4% |

Exemplary Lipstick Formulation

An example of a foundation composition is shown below in Table 4

TABLE 4

| Ingredient | Amount (wt %) |
|---|---|
| Alcohol | 0.0005-0.0015 |
| Butylparaben | 0.00001-0.00005 |
| Camellia sinensis leaf extract | 0.001-0.004 |
| Carmine | 0.05-0.15 |
| D&C Red No. 30 lake | 0.1-0.3 |
| D&C Red No. 7 | 0.05-0.20 |
| Dimethicone | 5-15 |
| Disteardimonium hectorite | 1-4 |
| Ethylparaben | 0.00001-0.00003 |
| FD&C yellow No.5 aluminum lake | 0.1-0.3 |
| Flavor | 0.1-0.3 |
| Glycerin | 0.001-0.004 |
| Isododecane | 50-60 |
| Methylparaben | 0.00005-0.00009 |
| Mica | 5-9 |
| Phenoxyethanol | 0.0001-0.0004 |
| Propylene carbonate | 0.5-3 |
| Propylene glycol | 0.05-0.15 |
| Propylparaben | 0.05-0.20 |
| Simmondsia chensis (jojoba) seed oil | 0.05-0.2 |
| Talc | 0.15-0.5 |
| Titanium dioxide | 0.5-2.5 |
| Tocopheryl acetate | 0.05-0.20 |
| Trimethyl siloxysilacate | 15-25 |
| water | 0.001-0.004 |

Exemplary Mascara Formulations

An example of a mascara composition that includes sepiolite clay is provided below in Table 5.

TABLE 5

| INCI NAME | WT % |
|---|---|
| AQUA/WATER/EAU | 50-55 |
| ACRYLATES COPOLYMER | 5-9 |
| GLYCERYL STEARATE | 5-8 |
| IRON OXIDES | 6-10 |
| Sepiolite | 2-5 |
| PROPYLENE GLYCOL | 1-4 |
| STEARIC ACID | 1-4 |
| COPERNICIA CERIFERA CERA/COPERNICIA CERIFERA (CARNAUBA) WAX/CIRE DE CARNAUBA | 1-4 |
| TRIETHANOLAMINE | 1-3 |
| POLYETHYLENE | 1-3 |
| LECITHIN | 1-3 |
| PROPYLENE CARBONATE | 1-3 |
| SYNTHETIC WAX | 0.5-3 |
| OLEIC ACID | 0.5-2 |
| ALCOHOL DENAT. | 0.5-2 |
| BENZYL ALCOHOL | 0.3-1 |
| ASCORBYL PALMITATE | 0.2-0.7 |
| TOCOPHEROL | 0.1-0.5 |
| PANTHENOL | 0.1-0.4 |
| PHENOXYETHANOL | 0.1-0.4 |
| METHYLPARABEN | 0.1-0.4 |
| ETHYLPARABEN | 0.1-0.4 |
| SODIUM LAURETH SULFATE | 0.05-0.4 |
| PROPYLPARABEN | 0.05-0.3 |
| GLYCINE SOJA (SOYBEAN) OIL | 0.05-0.3 |
| TRISODIUM EDTA | 0.05-0.2 |
| XANTHAN GUM | 0.03-0.2 |

TABLE 5-continued

| INCI NAME | WT % |
|---|---|
| SIMETHICONE | 0.01-0.2 |
| POTASSIUM SORBATE | 0.03-0.1 |
| TOCOPHERYL ACETATE | 0.02-0.09 |
| TETRASODIUM EDTA | 0.005-0.03 |
| AMMONIUM HYDROXIDE | 0.005-0.02 |
| METHYLCELLULOSE | 0.001-0.005 |
| BENZOIC ACID | 0.0001-0.001 |
| SORBIC ACID | 0.0001-0.0009 |
| SULFURIC ACID | 0.0001-0.0005 |

Another example of an exemplary mascara is shown below in Table 6.

TABLE 6

| INCI NAME | WT % |
|---|---|
| C11-12 ISOPARAFFIN | 60-70 |
| POLYETHYLENE | 5-10 |
| IRON OXIDES | 5-9 |
| Sepiolite | 5-10 |
| COPERNICIA CERIFERA CERA/COPERNICIA CERIFERA (CARNAUBA) WAX/CIRE DE CARNAUBA | 1-5 |
| TRIHYDROXYSTEARIN | 1-4 |
| PROPYLENE CARBONATE | 1-4 |
| PENTAERYTHRITYL HYDROGENATED ROSINATE | 1-4 |
| GLYCERYL ROSINATE | 0.5-3 |
| PHENOXYETHANOL | 0.3-0.7 |
| PROPYLPARABEN | 0.05-0.5 |
| TOCOPHERYL ACETATE | 0.03-0.08 |
| PANTHENOL | 0.03-0.08 |
| SORBITOL | 0.0005-0.008 |

Another example of an exemplary mascara is shown below in Table 7.

TABLE 7

| INCI | WT % |
|---|---|
| SODIUM LAURETH-12 SULFATE | 0.03-0.09 |
| HYDROLYZED COLLAGEN (DERIVED FROM FISH) | 0.01-0.05 |
| PANTOLACTONE | 0.005-0.009 |
| HYDROLYZED KERATIN | 0.001-0.006 |
| SODIUM SULFATE | 0.0005-0.004 |
| DISODIUM PHOSPHATE | 0.0005-0.003 |
| POLYSORBATE 60 | 0.0005-0.003 |
| POTASSIUM SORBATE | 0.0001-0.0005 |
| SODIUM PHOSPHATE | 0.0001-0.0005 |
| SODIUM BENZOATE | 0.00005-0.00009 |
| AQUA/WATER/EAU | 40-60 |
| CERA ALBA/BEESWAX/CIRE D'ABEILLE | 5-10 |
| AMMONIUM ACRYLATES COPOLYMER | 5-10 |
| IRON OXIDES | 6-10 |
| VP/EICOSENE COPOLYMER | 1-5 |
| PROPYLENE GLYCOL | 1-5 |
| CARNAUBA | 1-4 |
| CETYL ALCOHOL | 1-4 |
| POLYSORBATE 20 | 1-4 |
| ETHYLENE/ACRYLIC ACID COPOLYMER | 1-3 |
| ALCOHOL DENAT. | 1-4 |
| POTASSIUM CETYL PHOSPHATE | 1-4 |
| HYDROGENATED PALM GLYCERIDES | 1-4 |
| STYRENE/ACRYLATES COPOLYMER | 0.5-2 |
| STEARIC ACID | 0.5-2 |
| PHENOXYETHANOL | 0.5-1.4 |
| DISODIUM DECETH-6 SULFOSUCCINATE | 0.3-1.2 |
| PANTHENOL | 0.4-1 |
| Sepiolite | 0.1-0.6 |
| AMINOMETHYL PROPANOL | 0.1-0.8 |
| LAURETH-30 | 0.1-0.5 |
| C11-15 PARETH-7 | 0.1-0.4 |

TABLE 7-continued

| INCI | WT % |
|---|---|
| C11-15 PARETH-40 | 0.1-0.4 |
| TOCOPHERYL ACETATE | 0.1-0.4 |
| HYDROXYETHYLCELLULOSE | 0.05-0.3 |
| DISODIUM EDTA | 0.05-0.2 |
| ARGANIA SPINOSA KERNEL OIL | 0.05-0.2 |
| SODIUM DEHYDROACETATE | 0.04-0.1 |
| CAPRYLYL GLYCOL | 0.02-0.09 |

SUMMARY STATEMENTS

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A nail lacquer/polish composition comprising:
   at least one solvent,
   at least one primary film forming polymer,
   at least one pigment,
   a solvent based suspension of no more than about 2 wt percent of a complex of sepiolite clay intercalated with a mixture of monostearylbenzylammonium chloride and oleyldimethylbenzylammonium chloride, and
   about zero wt percent ester plasticizer, wherein the composition produces essentially little or no nitrosamine and the wt percentage is relative to the total weight of the composition with solvent.

2. A nail lacquer/polish composition of claim 1 wherein the pigment comprises solid pigment particles.

3. A nail lacquer/polish composition of claim 1, wherein the primary film forming polymer is a cellulosic polymer and/or a synthetic polymer.

4. A nail lacquer/polish composition of claim 1, further comprising a non-ester plasticizer selected from polyepoxide, C10-C30 fatty alcohol-polyepoxide of ethylene and/or propylene oxide, polyether of from about ten to fifty units of C2 to C4 alkyloxy moieties, a polyol, N-fatty alkyl tosylamide, fatty alkyl toluamide, aryl or alkyl sulfonamido polyether, aryl or alkyl sulfonamide and/or any combination thereof.

5. A nail lacquer/polish composition of claim 4 wherein the primary film forming polymer is cellulose acetate, cellulose acetate butyrate, ethyl cellulose, a vinyl polymer, nitrocellulose, an alkyl (meth)acrylate polymer or its copolymer with an alkene of 3 to 6 carbons and/or a styrene, and mixtures thereof.

6. A nail lacquer/polish composition of claim 5 wherein the primary film forming polymer is at least nitrocellulose.

7. A nail lacquer/polish composition of claim 1, further comprising at least one secondary film former comprising a poly(meth)acrylate, a copolymer of (meth)acrylate and olefin monomer, a polyurethane, a polyester, a polyamide, a polyimide, a polyurea, a polyol, an alkyd resin, a rosin resin, a toluene sulfonamide/epoxy resin, an arylsulfonamide, formaldehyde resin or any mixture thereof.

8. A nail lacquer/polish composition of claim 1, further comprising an organic dicarboxylic acid.

9. A nail lacquer/polish composition of claim 8 wherein the acidifying component is malic acid, citric acid, maleic acid or succinic acid.

10. A nail lacquer/polish composition of claim 9 wherein amount of organic dicarboxylic acid is minimal or essentially none.

11. A nail lacquer/polish composition of claim 1, wherein the weight average weight percentage of the mixture of monostearylbenzylammonium chloride and oleyldimethylbenzylammonium chloride relative to the weight average weight of the sepiolite clay is in a range of about 0.5 wt percent to about 8 wt percent, preferably about 0.5 wt percent to about 4 wt percent.

12. A nail lacquer/polish composition of claim 1, wherein the pigment includes at least solid colored organic compounds with amine groups.

13. A nail lacquer/polish composition of claim 1, further comprising one or more surfactants, metal flakes, curable resins, anti-foaming agents and/or leveling agents and mixtures thereof.

14. A nail lacquer/polish composition of claim 1, wherein the solvent is an organic solvent selected from one or more of ethyl acetate, methyl acetate, methanol, ethanol, isopropanol, diacetone alcohol, propyl acetate, n-butanol, xylene, amyl acetate, methyl ethyl ketone, acetone, methyl butyl ketone and mixtures thereof.

15. A nail lacquer/polish composition of claim 1, wherein the sepiolite clay is purified and dehydrated.

16. A nail lacquer/polish composition of claim 15 wherein the sepiolite clay is re-purified to remove impurities by slurrying in hot aqueous alcohol, filtering and drying.

17. A nail lacquer/polish composition of claim 16 wherein the re-purification is accomplished by dispersing sepiolite clay in a hot aqueous or aqueous-alcohol medium optionally and sequentially containing acid and base, cooling, filtering and drying under hot and optional vacuum conditions to provide purified sepiolite clay.

18. A method for use of a nail lacquer/polish composition of claim 1, comprising application of the composition onto finger and/or toe nails to form a wet coating and drying the wet coating to form a solid coating of colored lacquer/polish on the nails wherein the composition produces little or no nitrosamines while as a wet coating and/or while drying.

*     *     *     *     *